United States Patent [19]

Cherry et al.

[11] Patent Number: 5,057,496

[45] Date of Patent: Oct. 15, 1991

[54] DIPEPTIDE COMPOUNDS CONTAINING HISTIDINE OR N-METHYL HISTIDINE PROCESSES FOR THEIR PREPARATION AND COMPOSITIONS CONTAINING THEM

[75] Inventors: Peter C. Cherry; Michael W. Foxton, both of Chalfont St. Giles; Barry E. Ayres, Ickenham; Andrew D. Searle, Acton, all of England

[73] Assignee: Glaxo Group Limited, United Kingdom

[21] Appl. No.: 280,495

[22] Filed: Dec. 6, 1988

[30] Foreign Application Priority Data

Dec. 7, 1987 [GB] United Kingdom ............... 8728560

[51] Int. Cl.$^5$ .................... A61K 37/02; C07K 5/06
[52] U.S. Cl. .......................... 514/19; 546/194; 546/278
[58] Field of Search .............. 514/19; 546/194, 278

[56] References Cited

U.S. PATENT DOCUMENTS

| | | | |
|---|---|---|---|
| 4,533,656 | 8/1985 | Walker | 514/19 |
| 4,548,926 | 10/1985 | Matsueda et al. | 514/19 |
| 4,616,088 | 10/1986 | Ryono et al. | 548/344 |
| 4,665,193 | 5/1987 | Ryono et al. | 546/278 |
| 4,705,846 | 11/1987 | Thaisrivongs . | |
| 4,719,288 | 1/1988 | Fuhrer et al. | 548/495 |
| 4,746,649 | 5/1988 | Raddatz et al. | 514/19 |
| 4,749,687 | 6/1988 | Bindra et al. . | |

FOREIGN PATENT DOCUMENTS

| | | |
|---|---|---|
| 0184550 | 11/1985 | European Pat. Off. . |
| 0163237 | 12/1985 | European Pat. Off. . |
| 0173481 | 3/1986 | European Pat. Off. . |
| 0212903 | 3/1987 | European Pat. Off. . |
| 84/03044 | 8/1984 | World Int. Prop. O. . |
| 87/02581 | 5/1987 | World Int. Prop. O. . |
| 87/05302 | 9/1987 | World Int. Prop. O. . |

OTHER PUBLICATIONS

Burger, *Medicinal Chemistry*, 2nd Edition, Interscience Publishers, Inc., N.Y., pp. 565–601 (6/27/60).
Bolis et al., *Renin Inhibitors Dipeptide Analogues of Angiotensinogen Incorporating Transition-State, Nonpeptidic Replacements at the Scissile Bond,* J. Med. Chem., pp. 1729–1739, vol. 30, (1987).
Haber et al., *Renin Inhibitors: A Search for Principles of Design,* J. Cardiovascular Pharmacology, 10 (Supplement 7) pp. 554–558, (1987).

*Primary Examiner*—Lester L. Lee
*Attorney, Agent, or Firm*—Bacon & Thomas

[57] ABSTRACT

There are described new compounds of formula (1)

$$R^1-X^1-X^2-NH-\underset{\underset{CH_2R^2}{|}}{C}H-CH_2-\underset{\underset{}{|}}{\overset{\overset{OH}{|}}{C}}H-\underset{\underset{}{|}}{\overset{\overset{R^3}{|}}{C}}H-CONH-X^3-NR^4R^5 \quad (1)$$

wherein
$R^1$ represents an acyl group;
$X^1$ represents phenylalanine or p-methoxyphenylalanine bonded N-terminally to $R^1$ and C-terminally to $X^2$;
$X^2$ represents histidine or N-methylhistidine bonded N-terminally to $X^1$ and C-terminally to the group —NH—;
$R^2$ represents a $C_{4-6}$ cycloalkyl group;
$R^3$ represents a group $CHR^6R^7$ (where $R^6$ is a hydrogen atom or a hydroxyl group and $R^7$ is a pyridinyl ring);
$X^3$ represents a $C_{2-6}$ alkylene chain optionally substituted by one or more $C_{1-4}$ alkyl groups;
$R^4$, and $R^5$, which may be the same or different, each independently represent a hydrogen atom or a $C_{1-4}$ alkyl group, or $NR^4R^5$ may form a 5- or 6- membered polymethylenimine ring;
and salts and solvates thereof.

The new compounds have been found to exhibit activity as renin inhibitors, combining good duration of action with significant oral potency.

Compositions containing the compounds of formula (1) and processes for preparing the compounds are also described.

19 Claims, No Drawings

DIPEPTIDE COMPOUNDS CONTAINING HISTIDINE OR N-METHYL HISTIDINE PROCESSES FOR THEIR PREPARATION AND COMPOSITIONS CONTAINING THEM

This invention relates to a series of dipeptides which inhibit renin, to processes for their preparation, to pharmaceutical compositions containing them and to their use in medicine.

WO 84/03044 and EP-A-0173481 disclose compounds which are stated as useful as renin inhibitors. We have now found that a small group of dipeptides generically embraced by the very broad disclosures in the aforementioned patent specifications, but clearly outside the scope of the preferred embodiments described therein are highly active renin inhibitors having advantageous properties. In particular, the compounds of the present invention are highly selective inhibitors of the action of the natural enzyme renin. They also have a particularly advantageous combination of good duration of action with significant oral potency. Furthermore, the dipeptides of the present invention exhibit advantageous physico-chemical properties.

Thus, according to one aspect of the present invention, we provide the compounds of formula (1)

$$R^1-X^1-X^2-NH-CHCHCH_2CHCONH-X^3-NR^4R^5 \quad (1)$$
(with OH on first CH, $R^3$ on second substituted C, and $CH_2R^2$ branch)

wherein
$R^1$ represents an acyl group;
$X^1$ represents phenylalanine or p-methoxyphenylalanine bonded N-terminally to $R^1$ and C-terminally to $X^2$;
$X^2$ represents histidine or N-methylhistidine bonded N-terminally to $X^1$ and C-terminally to the group —NH—;
$R^2$ represents a $C_{4-6}$ cycloalkyl group;
$R^3$ represents a group $CHR^6R^7$ (where $R^6$ is a hydrogen atom or a hydroxyl group and $R^7$ is a pyridinyl ring);
$X^3$ represents a $C_{2-6}$ alkylene chain optionally substituted by one or more $C_{1-4}$ alkyl groups;
$R^4$ and $R^5$, which may be the same or different, each independently represent a hydrogen atom or a $C_{1-4}$ alkyl group, or $NR^4R^5$ may form a 5 or 6 membered polymethylenimine ring;
and salts and solvates (e.g. hydrates) thereof.

It will be appreciated that, for pharmaceutical use, the salts referred to above will be the physiologically acceptable salts, but other salts may find use, for example in the preparation of the compounds of formula (1) and the physiologically acceptable salts thereof.

Suitable salts of the compounds of formula (1) include acid addition salts formed with organic or inorganic acids (for example hydrochlorides, hydrobromides, sulphates, phosphates, nitrates, benzoates, naphthoates, hydroxynaphthoates, p-toluenesulphonates, methanesulphonates, sulphamates, ascorbates, oxalates, tartrates, salicylates, succinates, lactates, glutarates, glutaconates, acetates, trifluoroacetates, tricarballylates, citrates, fumarates and maleates).

It will also be appreciated that the compounds of formula (1) contain at least one undefined chiral centre (i.e. the carbon atom carrying the $R^3$ grouping) and the invention includes all individual optical isomers of the compounds of formula (1) as well as mixtures thereof. However, it is to be understood that the OH and $CH_2R^2$ groupings always retain the relative configurations shown in formula (1). It is to be further understood that the amino acid residues $X^1$ and $X^2$ always have the natural L-configuration.

References hereinafter to compounds of formula (1) and their use and preparation should, unless the context dictates otherwise, be taken to be references to the compounds and their salts, e.g. the physiologically acceptable salts.

In the compounds of formula (1), the 'acyl group' within the definition of $R^1$ may be, for example, a group $R^8X^4C(=O)$— where $R^8$ is a $C_{1-6}$ alkyl group and $X^4$ is an oxygen atom or a bond.

The term 'N-methylhistidine' within the definition of $X^2$ means a histidine group containing a methyl substituent attached to the amide nitrogen atom linking $X^1$ and $X^2$.

The pyridyl ring represented by $R^7$ may be attached to the rest of the molecule by the 2-, 3- or 4-position.

The term 'alkyl' as defined within $X^3$, $R^4$, $R^5$ and $R^8$ may be a straight or branched chain alkyl group. Examples of suitable alkyl groups include methyl, ethyl, n-propyl, i-propyl, n-butyl, s-butyl and t-butyl.

When $R^4$ or $R^5$ are alkyl groups or $X^3$ contains an alkyl substituent this is preferably methyl.

$R^1$ preferably represents the group $R^8X^4C(=O)$— where $R^8$ is a $C_{1-4}$ alkyl group and $X^4$ is an oxygen atom or a bond. Examples of such groups include acetyl, ethoxycarbonyl and t-butoxycarbonyl.

$R^2$ preferably represents a cyclopentyl group or, more preferably, a cyclohexyl group.

For the group $R^3$, $R^6$ represents a hydroxy group or more preferably a hydrogen atom and $R^7$ is preferably a pyridyl ring attached at the 3- or 4-position.

$X^3$ preferably represents a $C_{2-4}$ alkylene chain optionally substituted by one or two methyl groups. Examples of such chains include —(CH$_2$)$_2$—, —CH$_2$CH$_2$(CH$_3$)—, —CH$_2$C(CH$_3$)$_2$— and —(CH$_2$)$_4$—.

Preferably $R^4$ and $R^5$ each independently represent a hydrogen atom or a methyl group, more preferably each represent a hydrogen atom.

A preferred class of compounds of the invention are those represented by formula (1a)

$$R^1-X^1-X^2-NH-CHCHCH_2CHCONH-X^3-NR^4R^5 \quad (1a)$$
(with OH, $R^3$, and $CH_2$—cyclohexyl substituents)

wherein $R^1$ represents a group $R^8X^4C(=O)$— where $R^8$ is a $C_{1-4}$ alkyl group and $X^4$ is an oxygen atom or a bond; $X^1$, $X^2$ and $R^3$ are as defined in formula (1) above; $X^3$ represents a $C_{2-4}$ alkylene chain optionally substituted by one or two methyl groups; and $R^4$ and $R^5$ each represent a hydrogen atom or a methyl group.

A preferred group of compounds from within this preferred class are those in which $R^1$ represents an acetyl, ethoxycarbonyl or t-butoxycarbonyl group, $R^6$ represents an acetyl, ethoxycarbonyl or t-butoxycarbonyl group, $R^6$ represents a hydroxy group or more particularly a hydrogen atom, $R^7$ represents a pyridyl ring attached at the 3- or 4-position, $X^3$ represents a $C_{2-4}$ alkylene chain selected from —$(CH_2)_2$—, —$CH_2CH(CH_3)$—, —$CH_2C(CH_3)_2$— or —$(CH_2)_4$— and $R^4$ and $R^5$ each represent a hydrogen atom.

A further preferred group of compounds from within this preferred class are those in which $R^1$ represents an acetyl, ethoxycarbonyl or t-butoxycarbonyl group, $X^1$ represents phenylalanine or more particularly p-methoxyphenylalanine, $X^2$ represents histidine, $R^6$ represents a hydrogen atom and $R^7$ represents a pyridyl ring attached at the 3- or more particularly the 4-position, $X^3$ represents the chain —$(CH_2)_4$— and $R^4$ and $R^5$ each represent a hydrogen atom.

Particularly preferred compounds according to the invention are:

N-[5-[(4-aminobutyl)amino]-2S-hydroxy-5-oxo-1S-(cyclohexylmethyl)-4R-(4-pyridinylmethyl)-1-pentyl]-[N-[ethoxycarbonyl]-L-(O-methyl)-tyrosinyl]-L-histidinamide;

N-[5-[(4-aminobutyl)amino]-2S-hydroxy-5-oxo-1S-(cyclohexylmethyl)-4R-(4-pyridinylmethyl)-1-pentyl]-[N-[acetyl]-L-(O-methyl)tyrosinyl]-L-histidinamide;

N-[5-[(4-aminobutyl)amino]-2S-hydroxy-5-oxo-1S-(cyclohexylmethyl)-4R-(4-pyridinylmethyl)-1-pentyl]-[N-[(1,1-dimethylethoxy)carbonyl]-L-(O-methyl)-tyrosinyl]-L-histidinamide;

N-[5-[(4-aminobutyl)amino]-2S-hydroxy-5-oxo-1S-(cyclohexylmethyl)-4R-(4-pyridinylmethyl)-1-pentyl]-[N-[(1,1-dimethylethoxy)carbonyl]-L-phenylalanyl]-L-histidinamide and salts, especially physiologically acceptable salts, and solvates thereof.

Compounds of formula (1) have been shown both in vitro and in vivo to inhibit the action of the natural enzyme renin.

Human renin inhibitory potency was determined in vitro by measuring the ability of the test compound to inhibit endogenous plasma renin generation of angiotensin I from endogenous substrate at pH 7.4. Liberated angiotensin I was measured by an antibody-trapping radioimmunoassay technique based on methods described by K. Poulsen and J. Jorgensen in J. Clin. Endocrinol. Metab. (1974), 39, 816–825 and M. Szelke et al. in Hypertension (1982), 4, Suppl. II, 59–69.

Inhibition of plasma renin activity was also assessed in the conscious chronically-cannulated normotensive marmoset according to the method of C. J. Gardner and D. J. Twissell in Brit. J. Pharmacol. (1985), 86, 620P. Frusemide (5 mg/kg i.v.) was administered to the marmoset 30 minutes before the beginning of the experiment in order to elevate and stabilise renin levels. The plasma renin activity was measured according to the aforementioned procedure.

Compounds according to the invention may therefore be of particular use in the treatment of hypertension. They are also potentially useful for the treatment of other diseases such as hyperaldosteronism, cardiac insufficiency, congestive heart failure, post-myocardial infarction, cerebrovascular disorders, glaucoma and disorders of intracellular homeostasis.

Compounds according to the invention also have favourable physico-chemical properties. Thus, for example, compounds of the invention have good water solubility at near to physiological pH [e.g. pH 6.0 to 8.0] which makes them particularly suitable for parenteral administration.

According to a further aspect of the invention we provide a compound of formula (1) or a physiologically acceptable salt thereof for use in the treatment of the aforementioned diseases, especially hypertension.

According to another aspect of the invention we provide the use of a compound of formula (1) or a physiologically acceptable salt thereof for the manufacture of a therapeutic agent for the treatment of the aforementioned diseases, especially hypertension.

According to a further aspect of the invention we provide a method of treating the aforementioned diseases, especially hypertension, which method comprises administering an effective amount of a compound of formula (1) or a physiologically acceptable salt thereof to the patient.

It will be appreciated that the compounds of formula (1) may advantageously be used in conjunction with one or more other therapeutic agents, such as for example diuretics and/or different antihypertensive agents. It is to be understood that the present invention covers the use of a compound of formula (1) or a physiologically acceptable salt thereof in combination with one or more other therapeutic agents.

The compounds of the invention may be formulated in any convenient manner with one or more pharmaceutical carriers. Thus, a further aspect of the invention includes pharmaceutical compositions comprising a compound of formula (1) or a physiologically acceptable salt thereof formulated for oral, buccal, transdermal, parenteral or rectal administration or in a form suitable for administration by inhalation or insufflation. Oral administration is preferred.

For oral administration the pharmaceutical composition may take the form of for example tablets, which may be film or sugar coated, capsules, powders, granules, solutions including syrups, or suspensions prepared by conventional means with acceptable excipients.

For parenteral administration the compounds of formula (1) may be given as a bolus injection or by continuous infusion. The compositions may take such forms as suspensions, solutions or emulsions in oily or aqueous vehicles and may contain formulatory agents such as suspending, stabilising and/or dispersing agents. For administration by injection these may take the form of a unit dose presentation or as a multidose presentation preferably with an added preservative.

Alternatively for parenteral administration the active ingredient may be in powder form for reconstitution with a suitable vehicle.

The compounds of formula (1) may be formulated as ointments and creams for transdermal administration and as suppositories or retention enemas for rectal administration.

For buccal administration the composition may take the form of tablets or lozenges formulated in conventional manner.

For administration by inhalation the compounds according to the invention are conveniently delivered in the form of an aerosol spray presentation from pressurised packs with the use of a suitable propellant, e.g. dichlorodifluoromethane, trichlorofluoromethane, dichlorotetrafluoroethane, carbon dioxide or other suitable gas, or from a nebuliser. In the case of a pressurised aerosol the dosage unit may be determined by providing a valve to deliver a metered amount.

Alternatively, for administration by inhalation the compounds according to the invention may take the form of a dry powder composition, for example a powder mix of the compound and a suitable powder base such as lactose or starch. The powder composition may be presented in unit dosage form in, for example, capsules or cartridges of e.g. gelatin, or blister packs from which the powder may be administered with the aid of an inhaler or insufflator.

When the compositions comprise dosage units, each unit will preferably contain 5 mg to 500 mg, advantageously where the compounds are to be administered orally 25 mg to 400 mg of the active compound. The daily dosage as employed for adult human treatment will preferably range from 5 mg to 3 g, most preferably from 25 mg to 1 g which may be administered in 1 to 4 daily doses, for example, depending on the route of administration and on the condition of the patient.

The compounds of formula (1) may be prepared by the following processes, wherein the various groups and symbols are as defined for formula (1) unless otherwise specified.

Thus, according to a further aspect of the present invention, we provide a process for preparing the compounds of formula (1) which comprises treating the lactone of formula (2)

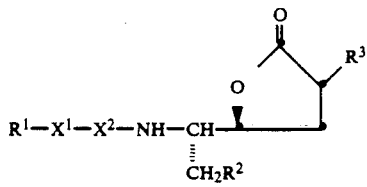

(2)

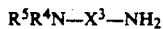

with a diamine of formula (3)

$R^5R^4N—X^3—NH_2$ (3)

and, if desired, followed by salt formation.

The reaction may be effected in the absence or presence of a solvent at any suitable temperature e.g. room temperature to 80° C. Suitable solvents include alcohols or halogenated hydrocarbons (e.g. dichloromethane).

It will be appreciated that when $R^4$ and $R^5$ both represent hydrogen atoms it may be desirable to protect one of the two primary amino groups in the diamine (3) in order to effect the desired reaction. Suitable protecting groups include benzyloxycarbonyl or the primary amine may form a phthalimido group which may be removed using standard procedures.

Intermediates of formula (3) are either known compounds or may be prepared by methods analogous to those described for preparing the known compounds of formula (3).

The lactones of formula (2) may be prepared from compounds of formula (4)

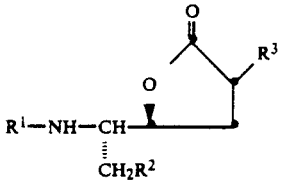

(4)

using well-known methods for introducing the amino acid residues $X^1$ and $X^2$.

Thus, for example, the compound (4) may be selectively hydrolysed e.g. with hydrogen chloride in dioxan or tetrahydrofuran or with trifluoroacetic acid to provide the compound (5)

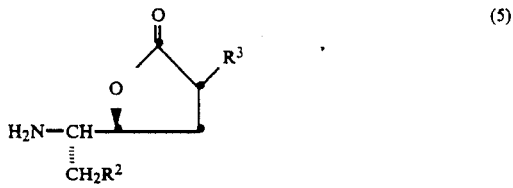

(5)

or a salt thereof (e.g. the hydrochloride salt).

The compound (5) or a salt thereof may then be treated with a carboxylic acid of formula (6)

$R^1—X^1—X^2—OH$ (6)

under dehydrating conditions to provide the desired intermediate of formula (2). The dehydration reaction may be effected in a suitable solvent (e.g. an amide such as dimethylformamide) in the presence of a dehydrating agent such as diphenylphosphoryl azide and preferably in the presence of a base such as triethylamine.

Alternatively, the compound (5) may be converted to the compound of formula (2) in a stepwise manner involving sequential reaction with the compounds of formulae (7) and (8)

$R^1—X^2—OH$ (7)

$R^1—X^1—OH$ (8)

or a suitable ester thereof, e.g. the pentafluorophenyl or 1-hydroxybenzotriazole ester.

Reaction with the compounds (7) and (8) may be effected under dehydrating conditions analogous to those described just above. Reaction with the pentafluorophenyl esters of the compounds (7) and (8) may be similarly effected but using an amine such as 4-(2-aminoethyl)morpholine in place of the dehydrating agent. Reaction with the 1-hydroxybenzotriazole esters of the compounds (7) and (8) may be similarly effected but using a base such as triethylamine in place of the dehydrating agent and optionally in the presence of a cosolvent such as a halohydrocarbon (e.g. dichloromethane).

It will be appreciated that the $R^1$ group will need to be removed after reaction with (7) and before reaction with (8). The $R^1$ group may be removed under acidic conditions as described previously.

It may be necessary to protect other active groupings in the molecule when preparing a compound of formula (2). Thus, for example, when the compound of formula (2) is prepared in a stepwise manner from a compound of formula (5) the histidine imidazole NH group may need to be protected. Suitable protecting groups include 2,4-dinitrophenyl which may subsequently be removed under the general process conditions described above for preparing compounds of formula (1) from compounds of formulae (2) and (3).1.

The compounds of formulae (6), (7) and (8) are either known compounds or may be prepared from known compounds using standard methodology.

The compounds of formula (4) may be prepared from compounds of formula (9)

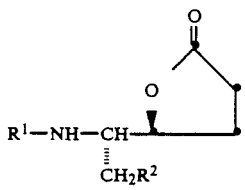

using methods for introducing the group $R^3$.

When $R^3$ represents $-CH(OH)R^7$ the conversion may be effected in a single step involving reacting the compound (9) with an aldehyde $R^7CHO$. The reaction takes place in a suitable solvent such as an ether (e.g. tetrahydrofuran) at a low temperature (e.g. $-70°$ C.) in the presence of a strong base e.g. sodium bistrimethylsilylamide.

When $R^3$ represents $-CH_2R^7$ the conversion may be effected by the following sequence of reactions:

If a salt of a compound of formula (1) is formed, the corresponding base may be obtained by addition of a suitable base.

If a compound of formula (1) is obtained as a base, a corresponding salt may be obtained by conventional means, e.g. by addition of an appropriate acid. The reaction may conveniently be effected in a suitable solvent at room temperature.

A salt of a compound of formula (1) may be converted into a different salt, e.g. a physiologically acceptable salt by addition of a suitable acid using conventional means.

The general process steps described above may yield the product of general formula (1) as an individual stereoisomer. However, when for example $R^3$ and/or $X^3$ contains a chiral centre the product of general formula (1) may be obtained as an individual stereoisomer or as a mixture of stereoisomers. Specific isomers may be separated at any convenient point in the overall synthe-

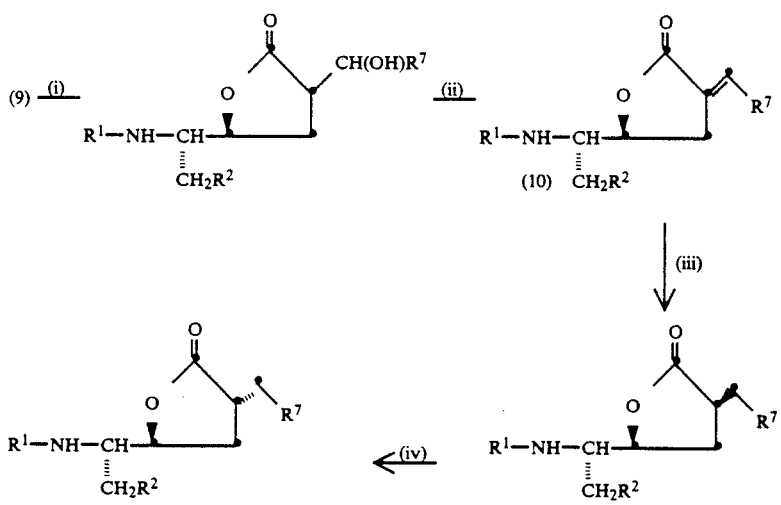

Step (i) involves the formation of a compound of formula (4) in which $R^3$ represents $-CH(OH)R^7$ using the method described above. Step (ii) may be effected by dehydration using a dehydrating agent such as N,N'-thiocarbonyldiimidazole in a solvent such as an ether (e.g. tetrahydrofuran) at an elevated temperature (e.g. reflux). Step (iii), a selective reduction, may be effected by hydrogenation using hydrogen in the presence of a transition metal catalyst (e.g. palladium) in a suitable solvent (e.g. acetic acid). The reaction provides the compounds of formula (4) in which the $-CH_2R^7$ group is in the (S) configuration. Step (iv) may be effected by treatment with sodium bistrimethylsilylamide at a low temperature (e.g. $-70°$ C.) in a suitable solvent such as an ether (e.g. acetic acid) and then by separation using chromatography. The reaction provides the compounds of formula (4) in which the $-CH_2R^7$ group is in the (R) configuration.

The compounds of formula (9) are either known compounds described in EP-A-0212903 or may be prepared according to the methods described therein for preparing the known compounds of formula (9).

Compounds of formulae (2), (4), (5) and (10) are novel, and the novel compounds form a further aspect of the present invention.

sis by conventional methods e.g. chromatography.

The following non-limiting Examples illustrate the invention. All temperatures are in °C.

INTERMEDIATE 1

3-[(4-Pyridinyl)hydroxymethyl]-5S-[1S-[[(1,1-dimethylethoxy)carbonyl]amino]-2-cyclohexylethyl]dihydrofuran-2-(3H)-one To a 1M solution of sodium bistrimethylsilylamide (67.4 ml), diluted with tetrahydrofuran (50 ml) and cooled to $-75°$ under nitrogen was added dropwise a solution of 5S-[1S-[[(1,1-dimethylethoxy) carbonyl]amino-2-cyclohexylethyl]dihydrofuran-2-(3H)-one (Compound A) (10 g) in tetrahydrofuran (100 ml), at a rate that maintained the reaction temperature below $-65°$. The resulting yellow solution was stirred at $-70°$ for 30 minutes, then a solution of 4-pyridinecarboxaldehyde (9 ml) in tetrahydrofuran (100 ml) was added over 1 minute. After stirring at $-70°$ for 45 minutes, acetic acid (3.9 ml), then water (300 ml) were added. The mixture was allowed to warm to 5°, when it was extracted with ethyl acetate (4×250 ml). The combined extracts were washed with water (2×100 ml), saturated brine (100 ml), dried (MgSO$_4$) and evaporated to a yellow gum. Chromatography on silica gel (1 kg), eluting with ethyl acetate/petrol (1:1 v/v) then ethyl acetate yielded the title compound as a white foam (5.8 g). NMR (DMSO-d6) δ 0.7-1.0 (2H,m), 1.0-1.8 (11H,m), 1.3-1.4 (9H,m), 2.1-2.2 (2H,m), 2.9-3.1 (1H,m), 3.5-3.7 (1H,m), 4.1-4.45 (1H,m), 4.95, 5.1 (1H,m), 7.3 and 7.4 (2H,dd), 8.5 (2H,dd).

Compound A is a known compound described in Example 3 in EP-A-0212903.

Intermediates 2 and 3 were prepared in a similar manner.

INTERMEDIATE 2

3-[(3-Pyridinyl)hydroxymethyl]-5S-[1S-[[(1,1-dimethylethoxy)carbonyl]amino]-2-cyclohexylethyl]dihydrofuran-2-(3H)-one (3.2 g)

NMR (DMSO-d6) δ 0.7-1.0 (2H,m), 1.0-1.8 (11H,m), 1.3-1.4 (9H,m), 2.0-2.3 (2H,m), 2.9-3.1 (1H,m), 3.5-3.7 (1H,m), 4.1-4.5 (1H,m), 5.0, and 5.1-5.2 (1H,m), 7.3-7.4 (1H,m), 7.7-7.8 (1H,m), 8.43-8.6 (2H,m).

IR (CHBr$_3$)$\nu_{max}$ 1710, 1760, 3430, 3600 cm$^{-1}$.

From Compound A (5 g) and 3-pyridinecarboxaldehyde.

INTERMEDIATE 3

3-[(2-Pyridinyl)hydroxymethyl]-5S-[1S-[[(1,1-dimethylethoxy)carbonyl]amino]-2-cyclohexylethyl]dihydrofuran-2-(3H)-one (2.08 g)

NMR (DMSO-d6) δ 0.7-1.0 (2H,m), 1.0-1.8 (11H,m), 1.4 (9H,s), 2.1-2.2 (2H,m), 3.2 (1H,m), 3.55-3.7 (1H,m), 4.1-4.3 (1H,m), 4.9 and 5.1 (1H,m), 7.2-7.3 (1H,m), 7.5 (1H,m), 7.7 (1H,m), 8.5 (1H,m).

From Compound A (5 g) and 2-pyridinecarboxaldehyde.

INTERMEDIATE 4

3-[(4-Pyridinyl)methylidene]-5S-[1S-[[(1,1-dimethylethoxy)carbonyl]amino]-2-cyclohexylethyl]dihydrofuran-2-(3H)-one A solution of Intermediate 1 (5.05 g) and N,N'-thiocarbonyldiimidazole (12.89 g) in tetrahydrofuran (100 ml) was heated under reflux for 24 h. The dark brown reaction mixture was concentrated in vacuo to give an oil which was purified by chromatography on silica gel (500 g), eluting with ethyl acetate/petrol (1:1 v/v) to yield the title compound (4.01 g). NMR (DMSO-d6) δ 0.7-1.0 (2H,m), 1.0-1.8 (11H,m), 1.22 (9H,s), 3.05-3.4 (2H,m), 3.7-3.8 (1H,m), 4.7 (1H,m), 6.88 (1H,d), 7.34 (1H,t), 7.55 (2H,d), 8.67 (2H,d).

Intermediates 5 and 6 were prepared in a similar manner.

INTERMEDIATE 5

3-[(3-Pyridinyl)methylidene]-5S-[1S-[[(1,1-dimethylethoxy)carbonyl]amino]-2-cyclohexylethyl]dihydrofuran-2-(3H)-one (2.50 g)

NMR (DMSO-d6) δ 0.7-1.0 (2H,m), 1.1-1.8 (11H,m), 1.23 (9H,m), 3.1-3.35 (2H,m), 3.7-3.9 (1H,m), 4.55-4.75 (1H,m), 6.9 (1H,d), 7.42 (1H,s), 7.5-7.6 (1H,dd), 8.05 (1H,d), 8.52 (1H,d), 8.83 (1H,s).

IR (Nujol($\nu_{max}$ 1692, 1750, 3220 cm$^{-1}$.

From Intermediate 2 (3.05 g).

INTERMEDIATE 6

3-[(2-Pyridinyl)methylidene]-5S-[1S-[[(1,1-dimethylethoxy)carbonyl]amino]-2-cyclohexylethyl]dihydrofuran-2-(3H)-one (0.5 g)

NMR (DMSO-d6) δ 0.7-1.0 (2H,m), 1.0-1.8 (11H,m), 1.22 (9H,s), 3.15-3.45 (2H,m), 3.6-3.8 (1H,m), 4.6-4.7 (1H,m), 6.88 (1H,d), 7.35-7.45 (2H,m), 7.7 (1H,d), 7.85-7.9 (1H,dt), 8.7 (1H,d).

From Intermediate 3 (0.87 g).

INTERMEDIATE 7

3S-[(4-Pyridinyl)methyl]-5S-[1S-[[(1,1-dimethylethoxy)carbonyl]amino]-2-cyclohexylethyl]dihydrofuran-2-(3H)-one A solution of Intermediate 4 (4.0 g) in acetic acid (40 ml) was treated with 10% palladium on charcoal (2 g), then stirred under an atmosphere of hydrogen for 2¾ h. The mixture was filtered through Kieselguhr, which was washed with acetic acid (200 ml). The filtrate and washings were concentrated in vacuo to give an orange gum. Chromatography on silica gel (200 g), eluting with ethyl acetate/petrol (2:1 v/v) yielded the title compound (3.7 g) as cream crystals. NMR (DMSO-d6) δ 0.7-1.0 (2H,m), 1.0-1.8 (12H,m), 1.38 (9H,s), 2.05-2.2 (1H,m), 2.6-2.75 and 3.05-3.1 (2H,abq), 3.2 (1H,m), 3.6-3.7 (1H,m), 4.3-4.4 (1H,m), 6.8 (1H,d), 7.25 (2H,d), 8.50 (2H,d).

Intermediates 8 and 9 were prepared in a similar manner.

INTERMEDIATE 8

3S-[(3-Pyridinyl)methyl]-5S-[1S-[[(1,1-dimethylethoxy)carbonyl]amino]-2-cyclohexylethyl]dihydrofuran-2-(3H)-one (2.24 g)

NMR (DMSO-d6) δ 0.7-1.0 (2H,m), 1.0-1.95 (12H,m), 1.4 (9H,s), 2.0-2.2 (1H,m), 2.6-2.8 (1H,q), 3.0-3.2 (2H,m), 3.55-3.7 (1H,m), 4.2-4.4 (1H,m), 6.83 (1H,d), 7.3-7.4 (1H,dd), 7.6-7.7 (1H,d), 8.48 (2H,s).

IR (CHBr$_3$)$\nu_{max}$ 1708, 1765, 3430 cm$^{-1}$.

From Intermediate 5 (2.34 g).

INTERMEDIATE 9

3S-[(2-Pyridinyl)methyl]-5S-[1S-[[(1,1-dimethylethoxy)carbonyl]amino]-2-cyclohexylethyl]dihydrofuran-2-(3H)-one (0.44 g)

NMR (DMSO-d6) δ 0.7-1.0 (2H,m), 1.0-1.9 (12H,m), 1.35 (9H,s), 2.1-2.2 (1H,m), 2.75-2.9 (1H,q), 3.15-3.3 (2H,m), 3.55-3.7 (1H,m), 4.25-4.4 (1H,m), 6.8 (1H,d), 7.2-7.3 (2H,m), 7.7 (1H,dt), 8.5 (1H,d).

From Intermediate 6 (0.57 g).

INTERMEDIATE 10

3R-[(4-Pyridinyl)methyl]-5S-[1S-[[(1,1-dimethylethoxy)carbonyl]amino]-2-cyclohexylethyl]dihydrofuran-2-(3H)-one To a solution of Intermediate 7 (1.00 g) in tetrahydrofuran (20 ml), cooled to −70° under nitrogen was added dropwise over one minute a 1M solution of sodium bistrimethylsilylamide in tetrahydrofuran (5.2 ml). The resulting yellow solution was stirred at −70° for 5 minutes, then acetic acid (0.64 ml) and water (30 ml) were added. The mixture was allowed to warm to 10°, when it was extracted with ethyl acetate (4×50 ml). The combined extracts were washed with water (2×20 ml), saturated brine (20 ml), dried (MgSO$_4$) and evaporated to give a cream foam. Crystallisation from ethyl acetate/petrol gave unchanged starting material as white needles (0.38 g). The mother liquors were evaporated to a cream foam which was purified by chromatography on silica gel (300 g), eluting with ethyl acetate/petrol (1:1 v/v) to yield the title compound (0.25 g) as a white foam. NMR (DMSO-f6) δ 0.7-1.0 (2H,m), 1.0-1.8

(11H,m), 1.35 (9H,s), 1.9-2.1 (2H,m), 2.6-2.8 and 3.0-3.1 (2H,abq), 2.8-2.9 (1H,m), 3.6-3.7 (1H,m), 4.4 (1H,m), 6.9 (1H,d), 7.25 (2H,d), 8.5 (2H,d). Further elution gave more unchanged starting material (0.24 g).

Intermediates 11 and 12 were prepared in a similar manner.

INTERMEDIATE 11

3R-[(3-Pyridinyl)methyl]-5S-[1S-[[(1,1-dimethylethoxy)carbonyl]amino]-2-cyclohexylethyl]dihydrofuran-2-(3H)-one (0.1 g)

NMR (DMSO-f6) δ 0.7-1.0 (2H,m), 1.0-1.8 (11H,m), 1.35 (9H,s), 1.95-2.1 (2H,m), 2.65-2.8 and 3.0-3.1 (2H,abq), 2.85-2.95 (1H,m), 3.5-3.7 (1H,m), 4.8-4.9 (1H,m), 6.9 (1H,d), 7.3-7.4 (1H,dd), 7.6-7.7 (1H,d), 8.4-8.5 (2H,m).

From Intermediate 8 (0.5 g).

INTERMEDIATE 12

3R-[(2-Pyridinyl)methyl]-5S-[1S-[[(1,1-dimethylethoxy)carbonyl]amino]-2-cyclohexylethyl]dihydrofuran-2-(3H)-one (0.11 g)

NMR (DMSO-d6) δ 0.7-1.0 (2H,m), 1.0-1.8 (11H,m), 1.35 (9H,s), 1.95-2.15 (2H,m), 2.8-3.2 (3H,m), 3.6-3.7 (1H,m), 4.35-4.45 (1H,m), 6.9 (1H,d), 7.2-7.35 (2H,m), 7.7 (1H,dt) 8.5 (1H,d).

From Intermediate 9 (0.62 g).

INTERMEDIATE 13

3-[(4-Pyridinyl)hydroxymethyl]-5S-[1S-amino-2-cyclohexylethyl]dihydrofuran-2-(3H)-one, dihydrochloride Intermediate 1 (60 mg) was stirred with a 4M solution of hydrogen chloride in tetrahydrofuran (2 ml) for 45 minutes at room temperature, then evaporated to yield the title compound as a pale yellow solid (60 mg). NMR (DMSO-d6) δ 0.7-1.0 (2H,m), 1.0-2.0 (13H,m), 3.2-3.45 (3H,m), 4.5-4.65 (1H,m), 5.2-5.4 (1H,m), 8.1 (2H,dd), 8.2-8.4 (3H,s), 8.9 (2H,d).

INTERMEDIATE 14

N-[1S-[[3-(4-Pyridinyl)hydroxymethyl]-2-oxo-(3H)-dihydrofuran-5S-yl]-2-cyclohexylethyl]-[N-[(1,1-dimethylethoxy)carbonyl]-L-phenylalanyl]-L-histidinamide Diphenylphosphoryl azide (34 μl) and triethylamine (55 μl) were added to a solution of Intermediate 13 (55 mg) and [N-[(1,1-dimethylethoxy)carbonyl]-L-phenylalanyl]-L-histidine (53 mg) in dimethylformamide (1 ml) cooled in an ice-bath. The reaction mixture was stirred at ice-bath temperature for 4 h, at room temperature for 16 h, then added to water (10 ml) and extracted with ethyl acetate (4×10 ml). The combined extracts were washed with water (3×5 ml), saturated brine (10 ml), dried (MgSO4) and evaporated to give a yellow solid which was purified by preparation high performance liquid chromatography to yield the title compound (51 mg). Mass spectrum MH+ =703.

INTERMEDIATE 15

N-[1S-[3R-(4-pyridinylmethyl)-2-oxo(3H)-dihydrofuran-5S-yl]-2-cyclohexylethyl]-[N(im)-(2,4-dinitrophenyl)]-[(1,1-dimethylethoxy)carbonyl-]-L-histidinamide A solution of N(im)-(2,4-dinitrophenyl)-(1,1-dimethyethoxycarbonyl)-L-histidine (112 mg) in dichloromethane (5 ml) was treated with 1-hydroxybenzotriazole hydrate (36 mg) and dicyclohexylcarbodiimide (55 mg). After stirring for 30 minutes at room temperature the precipitated dicyclohexylurea was filter off leaving a yellow filtrate. Intermediate (10) (107 mg) was stirred with a 4M solution of hydrogen chloride in dioxan (6 ml) for 1 h at room temperature, then evaporated to give a cream solid. The solid was dissolved in dimethylformamide (3 ml) and then triethylamine (0.11 ml) and the filtrate made above were added. After stirring for 16 h at room temperature, the solution was diluted with ethyl acetate (15 ml) and washed with water (2×15 ml). The washings were back-extracted with ethyl acetate (10 ml), then the combined organic extracts were washed with saturated sodium bicarbonate (20 ml), saturated brine (20 ml), dried (MgSO4) and evaporated to give a brown oil. Purification by column chromatography on silica gel (20 g), eluting with chloroform/methanol (30:1 v/v) yielded the title compound (112 mg) as a yellow oil which slowly crystallized on standing. NMR (DMSO-d6) δ 0.7-1.0 (2H, m), 1.0-1.8 (11H,m), 1.35 (9H, s), 1.8-2.0 (2H,m), 2.6-3.0 (5H, m), 4.0 (1H, m), 4.2 (1H, m), 4.45 (1H, m), 6.85 (1H, d), 7.2 (1H, s), 7.23 (2H, d), 7.7 (1H, d), 7.95 (1H, d), 8.0 (1H, s), 8.45 (2H, d) 8.65 (1H, dd), 8.95 (1H, d).

EXAMPLE 1

N-[5-[(4-Aminobutyl)amino]-2S-hydroxy-5-oxo-1S-(cyclohexylmethyl)-4R-(4-pyridinylmethyl)-1-pentyl]-[N-[(1,1-dimethylethoxy)carbonyl]-L-phenylalanyl]-L-histidinamide Intermediate 10 (176 mg) was stirred with a 4M solution of hydrogen chloride in dioxan (5 ml) for 30 minutes at room temperature, then evaporated to give a pale cream solid. This was mixed with [N-[(1,1-dimethylethoxy)carbony]-L-phenylalanyl]-L-histidine (176 mg) in dimethylformamide (7 ml) and the resulting solution cooled in an ice-bath. Diphenylphosphoryl azide (113 μl) and triethylamine (183 μl) were added, and the reaction was stirred in an ice-bath for 4 h, then at room temperature for 16 h. The reaction mixture was then added to water (40 ml) and extracted with ethyl acetate (4×50 ml). The combined extracts were washed with water (3×20 ml ), saturated brine (20 ml), dried (MgSO4) and evaporated to give a yellow gum. This was treated with 1,4-diaminobutane (0.5 ml) at 50° for 30 minutes, then evaporated to afford a white solid, which was purified by preparative high performance liquid chromatography to yield the title compound (220 mg) as a white powder. NMR (DMSO-d6) δ 0.7-1.0 (2H,m), 1.0-1.8 (17H,m), 1.3 (9H,s), 2.6-3.15 (11H,m), 3.3 (1H,d), 3.7-3.8 (1H,m), 4.1-4.2 (1H, m), 4.65 (1H,m), 7.0 (1H,d), 7.2-7.3 (5H,s) 7.4 (1H,s) 7.45 (2H,d), 7.5 (1H,d), 7.7 (3H,s), 7.8-7.9 (1H,t), 8.3-8.4 (1H,d), 8.6 (2H,d), 9.0 (1H,s). Mass spectrum MH+ =775.

The products of Examples 2-10 were prepared in a similar manner.

EXAMPLE 2

N-[5-[(4-aminobutyl)amino]-2S-hydroxy-5-oxo-1S-(cyclohexylmethyl)-4R-(3-pyridinylmethyl)-1-pentyl]-[N-[(1,1-dimethylethoxy)carbonyl]-L-phenylalanyl]-L-histidinamide (47 mg)

NMR (DMSO-d6) δ 0.7-1.0 (2H,m), 1.0-1.8 (17H,m), 1.3 (9H,s), 2.6-3.2 (11H,m), 3.3 (1H,d), 3.75 (1H,m), 4.15 (1H,m), 4.65 (1H,m), 7.0 (1H,d), 7.1-7.3 (6H,m), 7.4 (1H,s), 7.5 (1H,m), 7.65-7.9 (4H,m), 8.32 (1H,d), 8.43

(1H,s), 8.5 (1H,s), 9.0 (1H,s). Mass spectrum MH+ =775.

From Intermediate 11 (44 mg) and 1,4-diaminobutane.

EXAMPLE 3

N-[5-[(2-Aminoethyl)amino]-2S-hydroxy-5-oxo-1S-(cyclohexylmethyl)-4R-(3-pyridinylmethyl)-1-pentyl]-[N-[(1,1-dimethylethoxy)carbonyl]-L-phenylalanyl]-L-histidinamide (73 mg NMR (DMSO-d6) δ 0.7–1.0 (2H,m), 1.0–1.8 (13H,m), 1.3 (9H,s), 2.5–3.2 (11H,m), 3.3 (1H,d), 3.75 (1H,m), 4.1–4.2 (1H,m), 4.6–4.7 (1H,m) 7.0 (1H,m), 7.0 (1H,d), 7.1–7.3 (6H,m), 7.4 (1H,s), 7.45–7.55 (2H,m), 7.7–7.9 (3H,s), 8.0 (1H,t), 8.35 (1H,d), 8.45 (1H,s), 8.55 (1H,d), 9.0 (1H,s). Mass spectrum MH+ =747.

From Intermediate 11 (50 mg) and 1,2-diaminoethane.

EXAMPLE 4

N-[5-[(4-Aminobutyl)amino]-2S-hydroxy-5-oxo-1S-(cyclohexylmethyl)-4R-(2-pyridinylmethyl-1-pentyl]-[N-[(1,1-dimethylethoxy)carbonyl]-L-phenylalanyl]-L-histidinamide (99 mg)

NMR (DMSO-d6) δ 0.7–1.0 (2H,m), 1.0–1.8 (17H,m), 1.3 (9H,s), 2.6–3.15 (11H,m), 3.3 (1H,d), 3.75 (1H,m), 4.15 (1H,m), 4.65 (1H,m) 7.0 (1H,d), 7.2–7.3 (5H,m), 7.4 (1H,s), 7.4–7.6 (2H,m), 7.7 (3h,s), 7.8 (1H,m), 7.95 (1H,t), 8.3 (1H,d), 8.6 (1H,d),

EXAMPLE 5

N-[5-[(N,N-dimethylaminoethyl)amino]-2S-hydroxy-5-hydroxy-5oxo-1S-(cyclohexylmethyl)-4R-(4-pyridinylmethyl)-1-pentyl]-[N-(1,1-dimethylethoxy) carbonyl]-L-phenylalanyl]-L-histidinamide (58 mg)

NMR (DMSO-d6) δ 0.7–1.0 (2H,m) 1.0–1.9 (13H,m), 1.35 (9H,s), 2.8 (6H,s), 2.7–3.4 (12H,m), 3.8 (1H,m), 4.15 (1H,m), 4.65 (1H,m), 7.05 (1H,d), 7.2–7.4 (5H,m) 7.42 (1H,s), 7.48 (2H,d), 7.55 (1H,d), 8.15 (1H,t), 8.4 (1H,d), 8.64 (2H,d), 9.05 (1H,s). Mass spectrum MH+32 775.

From Intermediate 10 (40 mg) and 2-(N,N-dimethylamino)ethylamine.

EXAMPLE 6

N-[5-[(2-aminopropyl)amino]-2S-hydroxy-5-oxo-1S-(cyclohexylmethyl)-4R-(4-pyridinylmethyl)-1-pentyl]-N-[(1,1-dimethylethoxy)carbonyl]-L-phenylalanyl]-L-histidinamide (50 mg)

MNR (DMSO-d6) δ 0.7–1.0 (2H,m), 0.8–0.95 (3H,dd), 1.0–1.9 (13H,m), 1.32 (9H,s), 2.55–3.4 (12H,m), 3.75 (1H,m), 4.15 (1H,m), 4.65 (1H,m), 7.0 (1H,d), 7.15–7.35 (5H,m), 7.4 (1H,s), 7.5 (2H,d), 8.3 (3H,s), 8.1 (1H,s), 8.35 (1H,s), 8.6 (2H,d), 9.0 (1H,s). Mass spectrum MH+ =761.

From Intermediate 10 (40 mg) end 1,2-diaminopropane.

EXAMPLE 7

N-[5-[(2-amino-2-methylpropyl)amino]-2S-hydroxy-5-oxo-1S-(cyclohexylmethyl)-4R-(4-pyridinylmethyl)-1-pentyl]-N-[(1,1-dimethylethoxy) carbonyl]-L-phenylalanyl]-L-histidinamide (57 mg)

NMR (DMSO-d6) δ 0.7–1.0 (2H,m), 1.0 (6H,d), 1.0–1.8 (13H,m), 1.30 (9H,s), 2.6–3.2 (9H,m), 3.35 (1H,d), 3.8 (1H,m), 4.15 (1H,m), 4.65 (1H,m), 7.0 (1H,d), 7.15–7.35 (5H,m), 7.4 (1H,s), 7.45 (2H,d), 7.75–7.85 (3H,s), 8.1 (1H,t), 8.3 (1H,d), 8.6 (2H,d), 9.0 (1H,s). Mass spectrum MH+ =775.

From Intermediate 10 (40 mg) and 2,1-diamino-2-methylpropane.

EXAMPLE 8

N-[5-[(4-Aminobutyl)amino]-2S-hydroxy-5-oxo-1S-(cyclohexylmethyl)-4R-(4-pyridinylmethyl)-1-pentyl]-[N-[(,1,-dimethylethoxy)carbonyl]-0-methyl)-L-tyrosinyl]-L-histidinamide (74 mg)

NMR (DMSO-d6) δ 0.7–1.0 (2H,m), 1.0–1.8 (17H,m), 1.3 (9H,s), 2.55–3.15 (11H,m), 3.3 (1H,d), 3.72 (3H,s), 3.7–3.8 (1h,m), 4.0–4.1 (1H,m), 4.6–4.7 (1H,m), 6.8 (2H,d), 6.93 (1H,d), 7.15 (2H,d), 7.4 (1H,s). Mass spectrum MH+ =805.

From Intermediate 10 (62 mg), [N-[(1,1-dimethylethoxy)carbonyl]-L-(0-methyl)tyrosinyl]-L-histidine and 1,4-diaminobutane.

EXAMPLE 9

N-[5-[(4-Aminobutyl)amino]-2S-hydroxy-5-oxo-1S-(cyclohexylmethyl)-4R-( 4-pyridinylmethyl)-1-pentyl]-[N-[(1,1-dimethylethoxy)-carbonyl]-L-phenylalanyl-N-methyl]-L-histidinamide (59 mg).

NMR (DMSO-d6) δ 0.7–1.0 (2H,m), 1.0–1.8 (17H,m) 1.28, 1.36 (9H,ds), 2.61, 2.97 (3H,ds), 2.6–3.2 (11H,m), 3.3 (1H,m), 3.65–3.8 (1H,m), 4.4–4.5 (1H,m), 4.8–5.0 (1H,m), 5.2–5.4 (1H,m), 7.1 (1H,d), 7.1–7.3 (5H,m) 7.35 (1H,s), 7.45–7.55 (2H,dd), 7.65–7.8 (3H,s), 7.9 (1H,t), 8.6–8.8 (2H,m), 8.98 (1H,ds). Mass spectrum MH+ =789.

From Intermediate 10 (63 mg), [N-[1,1-dimethylethoxy)carbonyl]-L-phenylalanyl-N-methyl]-L-histidine and 1,4-diaminobutane.

EXAMPLE 10

N-[5-[(4-Aminobutyl)amino[-2S-hydroxy-5-oxo-1S-(cyclohexylmethyl)-4R-(4-pyridinylmethyl)-1-pentyl]-[N-[ethoxycarbonyl]-L-(0-methyl)tyrosinyl]-L-histidinamide (255 mg)

NMR (DMSO-d6) δ 0.7–1.0 (2H, m), 1.0–1.8 (17H, m) 1.1 (3h, t) 2.6–3.2 (11H, m), 3.9 (2H, q), 4.1 (1H, m), 4.6 (1H, m), 6.85 (2H, d), 7.2 (2H, d), 7.3 (1H, d), 7.4 (3H, m), 7.6–7.7 (3H, s), 7.85 (1H, t), 8.45 (1H, d), 8.6 (2H, d), 9.0 (1H, s). Mass spectrum MH+ =777.

From Intermediate 10 (244 mg), [N-[ethoxycarbonyl]-L-(0-methyl)tyrosinyl]-L-histidine and 1,4-diaminobutane.

EXAMPLE 11

N-[5-[(4-Aminobutyl)amino]-2S-hydroxy-5-oxo-1S(cyclohexylmethyl)-4-[(4-pyridinyl)hydroxymethyl]-1-pentyl]-[N-[(1,1-dimethylethoxy) carbonyl]-L-phenylalanyl]-L-histidinamide A solution of Intermediate 14 (15 mg) in 1,4-diaminobutane (0.2 ml) was kept at 40° for 1h, then evaporated to a gum, which was purified by preparative high performance liquid chromatography to give the title compound (14 mg). Mass spectrum MH+ =791.

The product of Example 12 was prepared in a similar manner.

EXAMPLE 12

N-[5-[(4-Aminobutyl)amino[-2S-hydroxy-5oxo-1S-(cyclohexylmethyl)-4-[(3-pyridinyl)hydroxymethyl]-1-pentyl]-[N-[(1,1-dimethylethoxy)carbonyl]-L-phenylalanyl]-L-histidinamide (162 mg)

NMR (DMSO-d6) δ 0.7–1.0 (2H,m), 1.0–1.8 (17H,m), 1.3 (9H,s), 2.55–3.15 (9H,m), 3.2–3.3 (1H,m), 3.6–3.7 and 3.9 (1H,m), 4.0–4.2 (1H,m), 4.55 (1H,m), 4.6 (1H,d), 6.95 (1H,d), 7.2–7.3 (5H,m), 7.35 91H,s), 7.45–7.55 (2H,m), 8.45–8.55 (2h,m), 9.0 (1H,s). Mass spectrum MH+ =791.

From Intermediate 2 (115 mg) in a one-pot synthesis.

EXAMPLE 13

N-[5-[(4-Aminobutyl)amino]-2S-hydroxy-5-oxo-1S-(cyclohexylmethyl)-4R-(4-pyridinylmethyl)-1-pentyl]-[N-[ethoxycarbonyl]-L-(0-methyl)tyrosinyl]-L-histidinamide A solution of ethoxycarbonyl(0-methyl)tyrosine (21 mg) in dichloromethane (2 ml) was treated with 1-hydroxybenzotriazole hydrate (10.5 mg) and dicyclohexylcarbodiimide (16 mg). After stirring for 30 minutes at room temperature the precipitated dicylcohexylurea was filtered off leaving a colourless filtrate. Intermediate 15 (55 mg) was stirred with a 5M solution of hydrogen chloride in dioxan for 1 h at room temperature then evaporated to give a brown solid. The solid was dissolved in dimethylformamide (2 ml) and treated with triethylamine (43 μl) and the filtrate from above. After stirring for 16 h at room temperature, the solution was diluted with ethyl acetate (10 ml), and washed with water (2×10 ml). The washings were back-extracted with ethyl acetate (10 ml), then the combined organic solutions washed with saturated sodium bicarbonate (2×10 ml), saturated brine (10 ml), dried (MgSO4) and evaporated to give a yellow solid. The solid was heated with 1,4-diaminobutane (1ml) at 50° for 30 minutes, then evaporated to give an orange solid, which was purified by preparative high performance liquid chromatography to yield the title compound (23 mg) as a pale yellow solid. NMR (DMSO-d6) δ 0.7–1.0 (2H, m), 1.0–1.8 (17H, m), 1.1 (3H, t), 2.6–3.2 (11H, m), 3.9 (2H, q), 4.1 (1H, m), 4.6 (1H, m), 6.85 (2H, d), 7.2 (2H, d), 7.3 (1H,d ), 7.4 (3H, m) 7.6–7.7 (3H, s), 7.85 (1H, t), 8.45 (1H, d), 8.6 (2h, d), 9.0 (1H, s). Mass spectrum MH+ =777.

EXAMPLE 14

N-[5-[(4-Aminobutyl)amino[-2S-hydroxy-5-oxo-1S-(cyclohexylmethyl)-4R-(4-pyridinylmethyl)-1-pentyl]-[N-[acetyl]-L-(0-methyl)tyrosinyl]-L-histidinamide A solution of acetyl(0-methyl)tyrosine (18.5 mg) in dichloromethane (2 ml) and dimethylformamide (1 drop) was treated with 1-hydroxybenzotriazole hydrate (10.5 mg) and dicyclohexylcarbodiimide (16 mg). After stirring for 1½ h at room temperature, the precipitated dicyclohexylurea was filtered off, leaving a colourless filtrate. Intermediate 15 (55 mg) was stirred with a 5M solution of hydrogen chloride in dioxan for 1 H at room temperature then evaporated to give a brown solid. The solid was dissolved in dimethylformamide (2 ml) and treated with triethylamine (43 μl) and the filtrate from above. After stirring for 16 h at room temperature, the solution was diluted with ethyl acetate (10 ml), and washed with water (2×10 ml). The washings were back-extracted with ethyl acetate (10 ml) then the combined organic solutions washed with saturated sodium bicarbonate (10 ml), saturated brine (10 ml), dried (MgSO4) and evaporated to give a yellow solid, which was then purified by preparative high performance liquid chromatography to yield the title compound (29 mg) as a yellow solid. NMR (DMSO-d6) δ 0.7–1.0 (2H, m), 1.0–1.8 (17H,m), 1.75 (3H, s), 2.6–3.2 (11H, m), 3.3 (1H, d), 4.3–4.4 (1H, m), 4.6 (1H, m), 6.8 (2H, d), 7.15 (2H, d), 7.35 (1h, s), 7.4 (2h, m),7.7 (3H, s), 7.85 (1H, s), 8.15 (1H, d), 8.5 (1H, d), 8.6 (2h, d), 9.0 (1H, s). Mass spectrum MH+ =747.

We claim:

1. A compound of formula (I)

$$R^1-X^1-X^2-NH-\underset{\overset{|}{CH_2R^2}}{CH}CHCH_2\underset{}{\overset{R^3}{\overset{|}{CH}}}CONH-X^3-NR^4R^5 \quad (1)$$

with OH on the first CH.

wherein

R$^1$ represents an acyl group;

X$^1$ is selected from phenylalanine and p-methoxyphenylalanine bonded N-terminally to R$^1$ and C-terminally to X$^2$;

X$^2$ is selected from histidine and N-methylhistidine bonded N-terminally to X$^1$ and C-terminally to the group —NH—;

R$^2$ represents a C$_{4-6}$ cycloalkyl group;

R$^3$ represents a group CHR$^6$R$^7$ (where R$^6$ is selected from hydrogen and hydroxyl and R$^7$ is a pyridinyl ring);

X$^3$ represents a C$_{2-6}$ alkylene chain optionally substituted by one or more C$_{1-4}$ alkyl groups;

R$^4$ and R$^5$, which may be the same or different, each independently selected from hydrogen and C$_{1-4}$ alkyl group, or NR$^4$R$^5$ forms a 5- or 6- membered polymethylenimine ring;

and salts and solvates thereof.

2. A compound of formula (I) as claimed in claim 1 wherein R$^1$ represents a group R$^8$X$^4$C(=O)—, wherein R$^8$ is a C$_{1-6}$ alkyl group and X$^4$ is an oxygen atom or a bond;

R$^2$ is selected from cyclopentyl and cyclohexyl;

R$^3$ represents a group —CHR$^6$R$^7$ wherein R$^6$ is selected from hydroxyl and hydrogen and R$^7$ represents a pyridyl ring attached at the 3-position or 4-position; X$^3$ represents a C$_{2-4}$ alkylene chain optionally substituted by one or two methyl groups; and R$^4$ and R$^5$ are each independently selected from hydrogen and methyl;

and salts and solvates thereof.

3. A compound of formula (Ia)

$$R^1-X^1-X^2-NH-\underset{\overset{|}{CH_2-\bigcirc}}{CH}CHCH_2CHCONH-X^3-NR^4R^5 \quad (Ia)$$

with OH and R$^3$ substituents.

wherein R$^1$ represents a group R$^8$X$^4$C(=O)—, where R$^8$ is a C$_{1-4}$ alkyl group and X$^4$ is an oxygen atom or a bond; X$^1$, X$^2$ and R$^3$ are as defined in formula (1) in claim 1; X$^3$ represents a C$_{2-4}$ alkylene chain optionally substituted by one or two methyl groups; and R$^4$ and $R^5$ are each independently selected from hydrogen and methyl; and salts and solvates thereof.

4. A compound as claimed in claim 3 wherein $R^1$ is selected from acetyl, ethoxycarbonyl and t-butoxycarbonyl group, $R^6$ is selected from hydroxyl and hydrogen, $R^7$ represents a pyridyl ring attached at the 3- or 4-position, $X^3$ represents a $C_{2-4}$ alkylene chain selected from $-(CH_2)_2-$, $-CH_2CH(CH_3)-$, $-CH_2C(CH_3)_2-$ and $-(CH_2)_4-$ and $R^4$ and $R^5$ each represent a hydrogen atom; and slats and solvates thereof.

5. A compound as claimed in claim 3 wherein $R^1$ is selected from an acetyl, ethoxycarbonyl and t-butoxycarbonyl group, $X^1$ is selected from phenylalanine and p-methoxyphenylalanine, $X^2$ represents histidine, $R^6$ represents a hydrogen atom and $R^7$ represents a pyridyl ring attached at the 3- or the 4-position, $X^3$ represents the chain $-(CH_2)_4-$ and $R^4$ and $R^5$ each represent a hydrogen atom; and salts and solvates thereof.

6. A compound of formula (I) as claimed in claim 1 selected from

N-[5-[(4-aminobutyl)amino[-2S-hydroxy-5-oxo-1S-(cyclohexylmethyl)-4R-(4-pyridinylmethyl)-1-pentyl]-[N-[ethoxy-carbonyl[-L-(O-methyl)-tyrosinyl]-L-histidinamide;

N-[5-[(4-aminobutyl)amino]-2S-hydroxy-5-oxo-1S-(cyclohexylmethyl)-4R-(4-pyridinylmethyl)-1-pentyl]-[N-[acetyl]-L-(O-methyl)tyrosinyl]-L-histidinamide;

N-[5-[(4-aminobutyl)amino]-2S-hydroxy-5-oxo-1S-(cyclohexylmethyl)-4R-(4-pyridinylmethyl)-1-pentyl]-[N-(1,1-dimethyl-ethoxy)carbonyl]-L-(O-methyl)-tyrosinyl]-L-histidinamide;

N-[5-[(4-aminobutyl)amino]-2S-hydroxy-5-oxo-1S-(cyclohexylmethyl)-4R-(4-pyridinylmethyl)-1-pentyl]-[N-[(1,1-dimethyl-ethoxy)carbonyl]-L-phenylalanyl]-L-histidinamide, and salts and solvates thereof.

7. The physiologically acceptable slats and solvates of a compound of formula (I) as claimed in claim 1.

8. A pharmaceutical composition comprising a compound of formula (I) as claimed in claim 1, or a physiologically acceptable salt or solvate thereof, in combination with a pharmaceutically acceptable carrier, diluent or excipient.

9. A process for preparing the compound of formula (1) as defined in claim 1 which comprises reacting a lactone of formula (2)

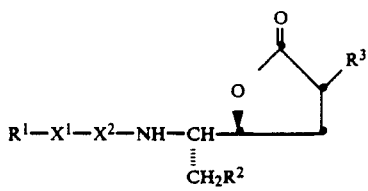

wherein $R^1$, $R^2$, $R^3$, $X^1$ and $X^2$ are as defined in claim 1, with a diamine of formula (3)

wherein $R^4$, $R^5$ and $X^3$ are as defined in claim 1, or a protected derivative thereof, followed if necessary or if desired, by removal of any protecting groups present and, if desired, by salt formation.

10. The physiologically acceptable salts and solvates of compounds of formula (Ia) as claimed in claim 3.

11. A process according to claim 9, wherein the process is carried out in the absence or presence of a suitable solvent at a temperature in the range of room temperature to 80° C.

12. A process according to claim 13 wherein an alcohol or a halogenated hydrocarbon is present as the solvent.

13. A pharmaceutical composition according to claim 8 wherein the compound of formula (I) is administered to an adult human in unit dosage form in a range of 5 mg to 3 g.

14. Compounds of formula (I) as defined in claim 1 wherein the salts are selected from the group consisting of hydrochlorides, hydrobromides, sulphates, phosphates, nitrates, benzoates, naphthoates, hydroxynapthoates, p-toluenesulphonates, methanesulphonates, sulphamates, ascorbates, oxalates, tartrates, salicylates, succinates, lactates, glutarates, glutaconates, acetates, trifluoroacetates, tricarballylates, citrates, fumarates and maleates, and wherein the solvates are hydrates.

15. Compounds as claimed in claim 2 wherein the salts are selected from the group consisting of hydrochlorides, hydrobromides, sulphates, phosphates, nitrates, benzoates, naphthoates, hydroxynapthoates, p-toluenesulphonates, methanesulphonates, sulphamates, ascorbates, oxalates, tartrates, salicylates, succinates, lactates, glutarates, glutaconates, acetates, trifluoroacetates, tricarballylates, citrates, fumarates and maleates, and wherein the solvates are hydrates.

16. Compounds as claimed in claim 3 wherein the salts are selected from the group consisting of hydrochlorides, hydrobromides, sulphates, phosphates, nitrates, benzoates, naphthoates, hydroxynapthoates, p-toluenesulphonates, methanesulphonates, sulphamates, ascorbates, oxalates, tartrates, salicylates, succinates, lactates, glutarates, glutaconates, acetates, trifluoroacetates, tricarballylates, citrates, fumarates and maleates, and wherein the solvates are hydrates.

17. Compounds as claimed in claim 4 wherein the salts are selected from the group consisting of hydrochlorides, hydrobromides, sulphates, phosphates, nitrates, benzoates, naphthoates, hydroxynapthoates, p-toluenesulphonates, methanesulphonates, sulphamates, ascorbates, oxalates, tartrates, salicylates, succinates, lactates, glutarates, glutaconates, acetates, trifluoroacetates, tricarballylates, citrates, fumarates and maleates, and wherein the solvates are hydrates.

18. Compounds as claimed in claim 5 wherein the salts are selected from the group consisting of hydrochlorides, hydrobromides, sulphates, phosphates, nitrates, benzoates, naphthoates, hydroxynapthoates, p-toluenesulphonates, methanesulphonates, sulphamates, ascorbates, oxalates, tartrates, salicylates, succinates, lactates, glutarates, glutaconates, acetates, trifluoroacetates, tricarballylates, citrates, fumarates and maleates, and wherein the solvates are hydrates.

19. A method of treating renin induced hypertension in a human or veterinary subject, which comprises administering to said subject an effective amount of a compound of formula (I) as claimed in claim 1.

* * * * *